United States Patent
Sullivan et al.

(10) Patent No.: US 7,694,822 B2
(45) Date of Patent: Apr. 13, 2010

(54) MEDICAL IMPLEMENT DISPOSAL AND COLLECTION DEVICE

(75) Inventors: Laurie Sullivan, Wellesley, MA (US); Robert A. Brown, Algonquin, IL (US); Anthony M. Sacchetti, Quincy, MA (US)

(73) Assignee: Covidien AG (CH)

( * ) Notice: Subject to any disclaimer, the term of this patent is extended or adjusted under 35 U.S.C. 154(b) by 1112 days.

(21) Appl. No.: 11/120,120

(22) Filed: May 2, 2005

(65) Prior Publication Data

US 2006/0243635 A1 Nov. 2, 2006

(51) Int. Cl.
*B65D 69/00* (2006.01)
*B65D 71/00* (2006.01)

(52) U.S. Cl. ...................... 206/571; 206/366

(58) Field of Classification Search ........... 206/571, 206/363–366, 229, 438; 312/209, 211; 220/578, 220/559; 222/386; 221/279; 232/43.1
See application file for complete search history.

(56) References Cited

U.S. PATENT DOCUMENTS

| | | | | |
|---|---|---|---|---|
| 516,961 | A * | 3/1894 | Boylan | 220/559 |
| 3,889,804 | A | 6/1975 | Ravich | |
| 4,588,093 | A * | 5/1986 | Field | 211/51 |
| 4,809,850 | A | 3/1989 | Laible et al. | |
| 5,084,028 | A * | 1/1992 | Kennedy et al. | 206/366 |
| 5,097,950 | A | 3/1992 | Weiss et al. | |
| 5,143,210 | A | 9/1992 | Warwick et al. | |
| 5,152,394 | A | 10/1992 | Hughes | |
| 5,251,783 | A | 10/1993 | Gringer | |
| 5,405,043 | A * | 4/1995 | Meloney | 220/578 |
| 5,494,158 | A | 2/1996 | Erickson | |
| 5,662,235 | A | 9/1997 | Nieto | |
| 5,706,942 | A | 1/1998 | Vila et al. | |
| 5,740,909 | A | 4/1998 | Nazare et al. | |
| 5,878,899 | A * | 3/1999 | Manganiello et al. | 220/578 |

(Continued)

FOREIGN PATENT DOCUMENTS

DE 538682 C 11/1931

(Continued)

OTHER PUBLICATIONS

International Search Report corresponding to Application No. PCT/US2006/016320 dated Sep. 29, 2006.

(Continued)

*Primary Examiner*—J. Gregory Pickett
(74) *Attorney, Agent, or Firm*—Lisa E. Winsor, Esq.

(57) ABSTRACT

A medical implement dispenser and disposal system is provided. The medical implement dispenser and disposal system comprises an enclosure having a body portion. A dispensing chamber within the body portion is configured to contain medical implements. A collection chamber within the body portion above the dispensing chamber is configured to collect soiled medical implements. The body portion defines an access opening positioned for passage of medical implements from the dispensing chamber and an inlet opening positioned for passage of soiled medical implements into the collection chamber, wherein the access opening is oriented in a forward facing direction and the inlet opening is also oriented in the forward facing direction. A barrier is positioned within the body portion to separate the dispensing chamber from the collection chamber. The barrier limits the passage of soiled medical implements from the collection chamber to the dispensing chamber.

17 Claims, 7 Drawing Sheets

U.S. PATENT DOCUMENTS

| | | |
|---|---|---|
| 6,685,017 B2 | 2/2004 | Erickson |
| 6,702,147 B2 | 3/2004 | Ashford |
| 2002/0190073 A1 | 12/2002 | Hewett |
| 2003/0132129 A1 | 7/2003 | Erickson |
| 2003/0226851 A1 | 12/2003 | Antebi |
| 2003/0226879 A1 | 12/2003 | Auclair et al. |

FOREIGN PATENT DOCUMENTS

| | | |
|---|---|---|
| DE | 9214287 U1 | 1/1993 |
| EP | 1449491 A | 8/2004 |
| GB | 2275673 A | 9/1994 |
| WO | WO 9101920 A2 | 2/1991 |
| WO | WO 2005/120610 A2 | 12/2005 |

OTHER PUBLICATIONS

International Search Report dated Sep. 1, 2006, application No. PCT/US2006/016736.

* cited by examiner

MEDICAL IMPLEMENT DISPOSAL AND COLLECTION DEVICE

FIELD OF THE INVENTION

The present invention relates to a disposal and collection device for medical implements.

BACKGROUND OF THE INVENTION

In a hospital, doctor's office or home environment setting, soiled syringes or other medical implements are commonly deposited in a disposal container following their use. Unused, sterile syringes or other medical implements are commonly obtained from a source separate from the disposal container. It is somewhat inconvenient at times, however, to provide a source of unused, sterile medical implements and a separate container for collecting the soiled medical implements following their use. In other words, it is sometimes disadvantageous from a convenience standpoint for medical practitioners to have one location from which implements are obtained and a separate location in which implements are disposed of.

Attempts have been made to overcome this inconvenience. For example, a syringe dispensing and storage container for personal use is disclosed by Erickson in U.S. Pat. No. 6,685, 017. U.S. Pat. No. 6,685,017 describes a syringe dispensing and collecting system comprising a multi-functional box and a plurality of unused syringes therein. The multi-functional box facilitates the sequential dispensing of unused syringes from the box, with concurrent facilitation of the safe sequential feeding of used syringes into the box for storage therein. A dividing tray is provided within the box to collect used syringes while simultaneously to provide a blockage between the used syringes and an exit opening.

Nevertheless, there continues to be a need to further develop and improve disposal and collection devices for medical implements.

SUMMARY OF THE INVENTION

According to an aspect of the invention, a medical implement dispenser and disposal system is provided. The medical implement dispenser and disposal system comprises an enclosure having a body portion. A dispensing chamber within the body portion is configured to contain medical implements. A collection chamber within the body portion above the dispensing chamber is configured to collect soiled medical implements. The body portion defines an access opening positioned for passage of medical implements from the dispensing chamber and the body portion further defines an inlet opening positioned for passage of soiled medical implements into the collection chamber, wherein the access opening is oriented in a forward facing direction and the inlet opening is also oriented in the forward facing direction. A barrier is positioned within the body portion to separate the dispensing chamber from the collection chamber. The barrier limits the passage of soiled medical implements from the collection chamber to the dispensing chamber.

According to another aspect of the invention, a secondary barrier is positioned above the barrier and is configured to collect the soiled medical implements to further limit the passage of soiled medical implements to the dispensing chamber.

According to yet another aspect of the invention, a method is provided for providing a supply of medical implements and a receptacle for soiled medical implements. The method comprises the step of positioning a barrier within an enclosure thereby dividing the enclosure into a collection chamber configured to collect soiled medical implements and a dispensing chamber configured to contain sterile medical implements. A secondary barrier is positioned within the collection chamber and above the barrier to collect the soiled medical implements and limit the passage of soiled medical implements from the secondary barrier to the dispensing chamber.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention. The invention is best understood from the following detailed description when read in connection with the accompanying drawing figures, which show exemplary embodiments of the invention selected for illustrative purposes. The invention will be illustrated with reference to the figures. Such figures are intended to be illustrative rather than limiting and are included herewith to facilitate the explanation of the present invention.

As used herein, the term medical implement refers to any commonly consumed device used for medical purposes, such as but not limited to a sharp, syringe, tongue depressor, lancet, scalpel, slide, pipette and the like.

Referring generally to the figures, a medical implement dispensing and disposal system according to exemplary aspects of this invention comprises an enclosure 100, 100', 200, 200', 300 having a body portion 110, 210, 310. A dispensing chamber 151, 251, 351 is provided or defined within the body portion 110, 210, 310 and is configured to contain medical implements. A collection chamber 150, 250, 350 is provided or defined within the body portion 110, 210, 310 above the dispensing chamber 151, 251, 351 and is configured to collect soiled medical implements.

The body portion 110, 210, 310 defines an access opening 123, 223, 323 positioned for passage of medical implements from the dispensing chamber 151, 251, 351 and an inlet opening 129, 229, 329 positioned for passage of soiled medical implements into the collection chamber 150, 250, 350, wherein the access opening 123, 223, 323 is oriented in a forward facing direction "D" and the inlet opening 129, 229, 329 is also oriented in the forward facing direction "D".

A barrier 115, 215, 315 is positioned within the body portion 110, 210, 310 to separate the dispensing chamber 151, 251, 351 from the collection chamber 150, 250, 350. The barrier limits the passage of soiled medical implements and contents thereof (e.g. biohazardous material waste and fluid) from the collection chamber to the dispensing chamber 151, 251, 351.

The soiled medical implements are collected in the collection chamber 150, 250, 350 within the enclosure 100, 100', 200, 200', 300. The unused, sterile medical implements are stored in the dispensing chamber 151, 251, 351 within the enclosure 100, 100', 200, 200', 300. The barrier tray 115, 215, 315 limits the passage of soiled medical implements from the collection chamber 150, 250, 350 to substantially prevent the contamination of the unused medical implements within the dispensing chamber 151, 251, 351. In response to the removal of unused medical implements from the dispensing chamber 151, 251, 351, the barrier tray 115, 215, 315, which sits above the unused medical implements, translates downward. As the barrier tray 115, 215, 315 translates downward, the volume of the collection chamber 150, 250, 350 increases thereby providing more available storage space for soiled medical implements.

A dispenser lid 120, 220 is positioned at the base of the dispensing chamber 151, 251, 351. The dispenser lid 120, 220 provides safe and controlled access to the unused medical implements. A collector lid 125, 225, 325 is positioned at the top of the collection chamber 150, 250, 350. The collector lid 125, 225, 325 facilitates the safe disposal of the soiled medical implements.

Figure 1:
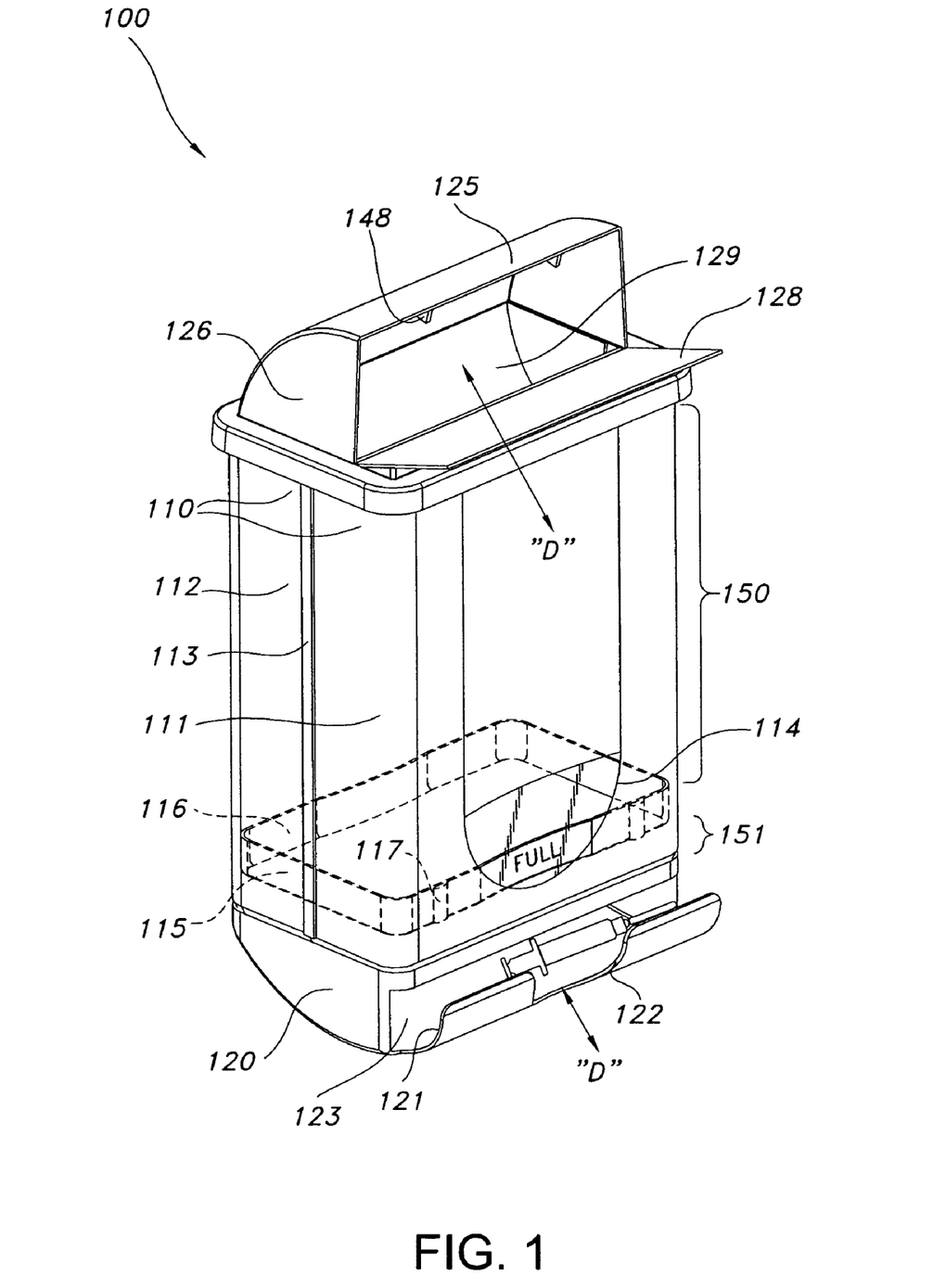
FIG. 1 is a front perspective view of an embodiment of a medical implement dispensing and disposal system according to an aspect of this invention.
Figure 2:
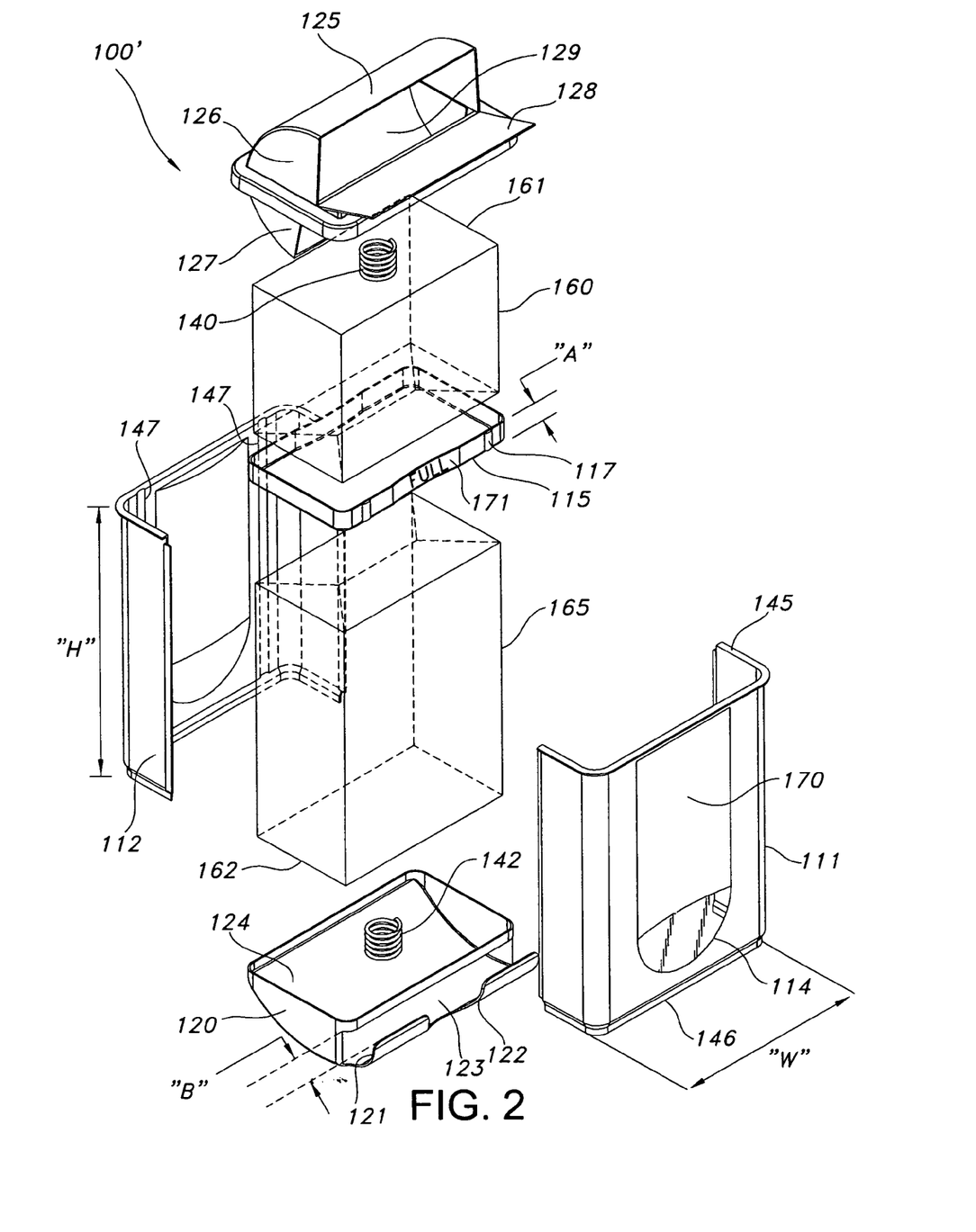
FIG. 2 is an exploded front perspective view of another embodiment of a medical implement dispensing and disposal system according to an aspect of this invention.

Referring specifically to the exemplary embodiments illustrated in FIGS. 1 and 2, a medical implement dispensing and disposal enclosure is generally designated by the numerals 100 and 100'. FIG. 1 provides a perspective view of an exemplary embodiment of the medical implement dispensing and disposal enclosure 100 configured to both store unused medical implements and collect soiled medical implements, herein referred to as enclosure 100. FIG. 2 is an exploded front perspective view of another exemplary embodiment of an enclosure 100' according to an aspect of this invention. The enclosure 100' illustrated in FIG. 2 is similar to the enclosure 100 illustrated in FIG. 1, however the enclosure 100' includes additional components to further limit the integration of sterile and soiled medical implements as well as facilitate the smooth translation of the barrier tray 115 along the body portion 110.

The enclosure 100, 100' of the exemplary embodiments generally includes a body portion 110, a barrier tray 115 positioned within the interior of the body portion 110, a collector lid 125 mounted to the top end of the body portion and a dispenser lid 120 mounted to the bottom end of the body portion 110. The barrier tray 115 serves as a divider between two distinct chambers of the body portion 110, i.e. a collection chamber 150 and a dispensing chamber 151. Soiled medical implements are collected within the collection chamber 150 and sterile medical implements are stored within the dispensing chamber 151.

In use, the enclosure 100, 100' is commonly employed in a hospital, doctor's office or home environment. The user removes one or more sterile medical implements from the dispenser lid 120 for use (e.g., for injection). By virtue of gravity, when the user removes the sterile medical implement(s) from the trough portion 121, the sterile medical implements within the dispensing chamber 151 are urged into the trough portion 121 of the dispenser lid 120 to fill the void left by the removed sterile medical implement(s). The barrier tray 115, which resides on top of the sterile medical implements, translates downward through the body portion 110 in response to the removal of the sterile medical implements from the dispensing chamber 151. Accordingly, the translation of the barrier tray 115 proportionately increases the available volume of the collection chamber 150. The now soiled medical implement(s) are inserted through the collector lid 125 for disposal. The soiled medical implement(s) descend through the collection chamber and settle on top of the barrier tray 115.

Regarding the medical implement distribution and disposal cycle, initially the dispensing chamber 151 is filled with unused medical implements, the collection chamber 150 is empty and the barrier tray 115 is positioned at or toward the top end of the body portion 110. At a midpoint of the cycle, the dispensing chamber 151 is partially filled with unused medical implements, the collection chamber 150 is partially filled with soiled medical implements and the barrier tray 115 is positioned in a central region of the body portion 110. At the end of the cycle, the dispensing chamber 151 is empty, the collection chamber 150 is filled with soiled medical implements and the barrier tray 115 is positioned at or toward the bottom end of the body portion 110.

Referring to the functionality and structure of the individual components of the exemplary embodiments illustrated in FIGS. 1 and 2, the body portion 110 provides the structural foundation of the enclosure 100, 100'. The walls of the body portion 110 are desirably thick enough to support the unused and soiled medical implements without significant deformation. To comply with industry standards (e.g. American Society for Testing and Materials), the walls of the body portion 100 are desirably composed of a puncture resistant material. The body portion 110 also retains the barrier tray 115 in a desired position and provides an optional lip or ridge for the mounting of the collector lid 125 and the dispenser lid 120. Although not shown, the collector lid 125 and the dispenser lid 120 may be coupled to the body portion 110 via chemical bond, friction welding or adhesive means.

The body portion 110 comprises a front casing 111 and a rear casing 112. The front casing 111 and the rear casing 112 interlock together to substantially seal the body portion 110 along two longitudinal seams 113. The front casing 111 and the rear casing 112 can be joined by a snap-fit joint, tongue and groove joint, pin-in-slot joint, adhesive, weld, clips, or any other mechanical fastening method commonly known in the art. The front casing 111 and the rear casing 112 can be virtually identical parts as shown in FIG. 1. Utilizing the same part for both the front casing 111 and the rear casing 112 reduces manufacturing, inventory and/or part tooling expenses. Alternatively, the front casing 111 and the rear casing 112 may be distinct parts, for example, to enhance the sealing characteristics of the enclosure or to incorporate a feature on only one of the casings.

Two lip portions 145, 146 are provided on the top end and bottom end of both casings 111, 112, respectively. The top lip portion 145 mates with a slot formed in the underside of the collector lid 125. The bottom lip portion 146 mates with a slot formed in the topside of the dispenser lid 120. The lip portions 145, 146 and the lids 125, 120, respectively, can be permanently or temporarily joined by a snap-fit joint, tongue and groove joint, pin-in-slot joint, adhesive, weld, clips, or any other mechanical fastening method commonly known in the art.

Two rails 147 extend along the height "H" of both casings 111, 112. The rails 147 may be notches (i.e. depressions) or rib protrusions formed in the casing 111, 112 walls. The rails 147 engage with a set of four flanges 117 positioned on the side walls 116 of the barrier tray 115. The flanges 117 of the barrier tray 115 maintain frictional contact with the rails 147. The flange-rail interface facilitates the smooth translation of the barrier tray 115 along the height "H" of the body portion 110. The flange-rail interface also substantially limits any twisting or distortion of the barrier tray 115. Other benefits of the barrier tray 115 will be described in further detail later.

Although not illustrated, the rear casing 112 may provide holes or protrusions to facilitate the mounting of the enclosure 100, 100' to a wall. For example, the rear casing 112 may incorporate a hole, slot, aperture, standoff, hook or other integral or attached feature to engage with a fastener on a wall. The rear casing 112 may also incorporate a series of clips or other protrusions to engage with a bracket mounted on a wall. It should be understood by one skilled in the art that numerous ways exist to mount the enclosure 100, 100' to a wall. The enclosure 100, 100' is not limited to wall mounting, as it may be transportable or oriented in an upright position on a table top.

In the exemplary embodiments illustrated in FIGS. 1 and 2, the body portion 110 is substantially opaque except for a window 114 that is partially or completely translucent or transparent. The window 114 cooperates with the barrier tray 115 for monitoring the content level of the chambers 150, 151. More specifically, the word "FULL" is printed or molded onto the side of the barrier tray 115. As the barrier tray 115 translates down the body portion 110 of the enclosure, the word "FULL" ultimately appears in the window 114 of the body portion 110. Accordingly, the user is thereby alerted that the collection chamber 150 is nearing its capacity and the dispensing chamber 151 is totally or substantially devoid of unused medical implements.

The window 114 may be a separate transparent component mounted to an opening formed in the body portion 110. Alternatively, the transparent window 114 may be integral with the body portion 110 and formed by a Co-Injection Molding Process. The integral transparent window 114 may also be generated by a surface finishing operation, e.g. Electro Discharge Machining (EDM).

The body portion 110 is optionally formed by an injection molding process. It should be understood by one skilled in the art that injection molded parts exhibit draft. To facilitate the smooth translation of the barrier tray 115 along the interior walls of the body portion 110 it is desirable for the interior walls to exhibit minimal draft. In other words, the width "W" of the body portion is desirably constant along the height "H" of the body portion 110. To overcome the challenges of draft, the body portion 110 of this exemplary embodiment comprises two separate components, i.e. the front casing 111 and the rear casing 112. By incorporating two separate components, neither front casing 111 nor rear casing 112 exhibit draft along the height "H", thereby facilitating the smooth translation of the barrier tray 115 along the body portion 110.

The barrier tray 115 of the exemplary embodiments separates the collection chamber 150 from the dispensing chamber 151 to substantially limit the passage of soiled medical implements and contents thereof into the dispensing chamber 151. The barrier tray 115 rests above the sterile medical implements within the dispensing chamber 151 and translates downward (by virtue of gravity) as the sterile medical implements are removed from the dispensing chamber 151.

The barrier tray 115 includes four flanges 117 positioned on the side walls 116. As described previously, the four flanges 117 engage with the body portion rails 147 to facilitate the smooth translation of the barrier tray 115 along the height "H" of the body portion 110. The flanges 117 may be integrally formed with the barrier tray 115 or the flanges 117 may be discrete components, such as an adhesive-backed spring clip currently sold by the Seastrom Corporation of Twin Falls, Id. USA. It would be desirable to utilize spring clips if the walls of the body portion 110 exhibit draft. In such case, the spring clips are configured to deflect to accommodate the varying width "W" of the body portion 110. The barrier tray 115 also includes a depression 171, which engages with a rail 170 formed on the interior of the body portion 110 to facilitate the translation of the barrier tray 115 along the body portion 110.

To further accommodate the smooth translation of the barrier tray 115 along the body portion 110, the height "A" of the side walls 116 is selectively sized to limit the barrier tray 115 from binding with the interior walls of the body portion 110. More particularly, the ratio of the height "A" of the side walls 116 to the width "$W_1$" of the barrier tray 115 (refer to FIG. 4) is tailored to limit the barrier tray 115 from seizing against the interior walls of the body portion 110. It was discovered that the smooth translation of the barrier tray 115 along the body portion 110 can be provided by increasing the height "A" of the side walls 116 while maintaining the width "$W_1$" of the barrier tray 115. The ratio of the height "A" of the side walls 116 to the width "$W_1$" of the tray 115 is greater than about 0.23:1 according to one exemplary embodiment of this invention. The ratio of the height "A" of the side walls 116 to the width "$W_1$" of the tray 115 is greater than about 0.25:1 according to another exemplary embodiment of this invention. For each of these ratios various heights "A" and widths "$W_1$" can be selected. The height "A" of the side walls 116 may refer to either the actual height of the side walls 116 as shown, or, alternatively, the height of the flanges 117 positioned on the side walls 116. Accordingly, the height of the flanges 117 may be any dimension greater or less than the side walls 116.

Although not shown, in another exemplary embodiment the flanges 117 extend both above and below the sidewalls 116 of the tray 115. In the event that the barrier tray 115 rotates, the portions of the flanges 117 extending above and below the sidewalls 116 make first contact with the rails 174 to limit the rotation of the tray 115.

The barrier tray 115 may be composed of either polypropylene, polyethylene or any other moldable material. A lubrication additive, such as Siloxane, may be added to the barrier tray 115 material to reduce the friction between the barrier tray 115 and the body portion 110.

Upon the disposal of the soiled medical implements, the soiled medical implements (sealed or unsealed) descend into the collection chamber 150 and collide with the barrier tray 115. It is contemplated that the soiled medical implements could feasibly pierce and therefore compromise the barrier tray 115. Accordingly, similar to the body portion 110, the barrier tray may be composed of a puncture resistant material to substantially prohibit the passage of soiled medical implements and contents thereof into the dispensing chamber 151. The barrier tray 115 may be formed by an injection molding or casting process. Alternatively, the barrier tray 115 may be formed from sheet-metal.

Although not shown, an absorbent pad configured to absorb soiled medical implement waste may be positioned directly above the barrier tray 115. The absorbent pad may be utilized in lieu of or in addition to the collection bag 160. The absorbent pad may be composed of a variety of known absorbent materials. If additional absorbency is needed or desired for a particular application, Super Absorbent Polymer (SAP) particles are optionally introduced into the absorbent pad. For example, one such pad is sold by Rayonier, Inc. under the NOVATHIN brand.

The dispenser lid 120 is mounted to the bottom end of the body portion 110, below the dispensing chamber 151. The dispenser lid 120 seals the bottom end of the enclosure 100, 100' and facilitates the controlled sequential distribution of the sterile medical implements. The sterile medical implements within the dispensing chamber 151 are urged through an access opening 123 and into the trough portion 121 of the dispenser lid 120 by the force of gravity. The trough portion 121 holds a limited number of medical implements at any time. As the user removes the medical implement(s) from the trough portion 121 of the dispenser lid 120, the medical implements within the dispensing chamber 151 are urged by the force of gravity into the trough portion 121 to fill the void left by the removed sterile medical implement(s). The base surface 124 of the dispenser lid is sloped to further urge the sterile medical implements out of the dispensing chamber 151 to ensure that all of the sterile medical implements are utilized.

The access opening 123 of the dispenser lid 120 is oriented in a forward facing direction "D" as shown in FIGS. 1 and 2. The access opening 123 is sufficiently sized to permit the emergence of the sterile medical implements from the dispensing chamber 151. The diameter "B" of the trough portion 121 is sufficient to accommodate a cylindrically shaped medical implement, such as a common sharp. Although the trough portion 121 can accommodate cylindrically shaped implements, the enclosure system is not limited to merely cylindrically shaped implements. The trough portion 121 provides an effective barrier to maintain the sterile medical implements in the dispensing chamber 151 while permitting controllable access to the sterile medical implements.

The trough portion 121 defines an access port 122 to provide user access to the dispensing chamber 151 through the access opening 123. If the medical implement(s) become trapped or stuck in the dispensing chamber 151 for any reason, the access port 122 provides adequate clearance for the user to reach into the dispensing chamber 151 to dislodge the trapped medical implement(s).

The dispenser lid 120 may be formed by an injection molding or casting process. The dispenser lid 120 may be integrated with the body portion 110 embodying a single component. The dispenser lid 120 may also be a discrete component separate from the body portion 110, as illustrated in FIG. 2. A dispenser lid 120 of the exemplary embodiment may be permanently mounted to the body portion 110 by welds, chemical bond or adhesive. Conversely, the discrete dispenser lid 120 may be removably mounted to the body portion 110 in order to replenish the supply of sterile medical implements within the dispensing chamber 151.

A collector lid 125 is mounted to the top end of the body portion 110, above the collection chamber 150. The collector lid 125 covers the top end of the enclosure 100, 100' to limit access to the soiled medical implements within the collection chamber 150 for safety purposes. The collector lid 125 defines an inlet opening 129 through which the soiled medical implements are deposited.

The collector lid 125 mounts to the top lip portion 145 of the body portion 110. The collector lid 125 can either be permanently or removably mounted to the body portion 110 by any mechanical fastening method commonly known in the art. The collector lid 125 includes a hood portion 126 and a cowl portion 127. The relative orientations of the hood portion 126 and cowl portion 172 establish a tortuous path. More specifically, the relative orientations of the hood portion 126 and cowl portion 172 substantially prevent a user from reaching through the inlet opening 129 of the collector lid 125 and into the collection chamber 150 to touch or remove a soiled medical implement.

The inlet opening 129 of the collector lid 125 is oriented in a forward facing direction "D" along with the access opening 123 of the dispenser lid 120, as illustrated in FIG. 1. It is advantageous to have both openings 123, 129 facing the same direction from a clearance standpoint since the enclosure 100, 100' is optionally configured to mount to a wall. By virtue of the orientation of the openings 123, 129, the enclosure 100, 100' may be positioned directly adjacent to another enclosure 100, 100' or any other object mounted on the wall, e.g. a cabinet or shelf. In a doctor's office or hospital setting it may be desirable to mount several enclosures 100, 100' onto a wall, adjacent to one another. For example, each enclosure mounted onto the wall at a hospital may contain a different type of medical implement. It is also advantageous to maintain the openings 123, 129 in the forward facing direction "D", so that the medical implements are facing the user. Although the enclosure 100, 100' is configured to mount to a wall, the enclosure 100, 100' is not limited to wall mounting, as the enclosure 100, 100' may be transportable or oriented in an upright position on a table top.

The collector lid 125 is optionally provided with a gate 128 to restrict access to the collection chamber 151. The gate 128 pivots about an axis (not shown) to either a closed or open position. The gate 128 is shown in the open position in FIGS. 1 and 2. In the closed position, the gate 128 covers all or a portion of the inlet opening 129 to restrict access to the collection chamber 151. In use, the gate 128 is closed by pivoting the gate 128 about its axis. The gate 128 flexes as it travels along and engages with a rib 148 formed in the hood portion 126. The gate 128 eventually pivots past the rib 148 and locks into place. The rib 148 limits the gate 128 from pivoting back to an open position. The gate 128 may be used, for example, to restrict access to the collection chamber 151 once the collection chamber 151 is full or the gate 128 may be used to limit leakage during transportation.

Although only a single collector lid 125 is selected for illustration, other collector lids are contemplated for use with the enclosure 100, 100'. For example, other collector lids are described by Ponsi et al. in U.S. Pat. No. 6,387,735, which is incorporated herein by reference and by Gaba et al. in U.S. Pat. No. 5,947,285, which is also incorporated herein by reference. Conversely, a single opening positioned at the top end of the enclosure 100, 100' may be provided in lieu of the discrete collector lid 125.

Referring now to the exemplary embodiment illustrated in FIG. 2, the enclosure 100' includes an optional collection bag 160. The collection bag 160 is utilized in addition to the barrier tray 115 to further limit the passage of soiled medical implements and contents thereof to the dispensing chamber 151. The soiled medical implements disposed through the inlet opening 129 of the collector lid 125 are collected in the collection bag 160. Accordingly, a single open face 161 of the collection bag 160 is oriented as shown to accept soiled medical implements from the inlet opening 129 of the collector lid 125. The utilization of the collection bag 160 may facilitate the reuse of the enclosure 100', which is at the option of the end user. In use, a full collection bag 160 may be removed and replaced with a new collection bag 160. The reuse of the enclosure 100' may represent a cost savings to the end user.

The collection bag 160 is either permanently affixed or temporarily attached to either the collector lid 125 or the body portion 110. For example, the periphery of the open face 161 of the collection bag 160 may be sandwiched between the top lip portion 145 and the underside of the collector lid 125 to facilitate the ready removal of the bag 160. Alternatively or in addition to sandwiching the bag 160, the collection bag 160 may be welded or adhered and thereby sealed to the body portion 110.

It is contemplated that the soiled medical implements could possibly pierce and therefore compromise the collection bag 160. Accordingly, the collection bay 160 may be composed of a puncture resistant material to substantially prohibit the passage of soiled medical implements and contents thereof through the collection bag 160. The collection bag 160 is desirably composed of a collapsible and flexible material capable of molding to the varying shape of the collection chamber 150. In this exemplary embodiment, the collection bag 160 is formed from 1 mil thick polyethylene, although the bag material is not limited to one particular material type or thickness.

The enclosure 100' also includes an optional isolation bag 165, as illustrated in FIG. 2. The isolation bag 165 is utilized in addition to the collection bag 160 and the barrier tray 115 to further limit the passage of soiled medical implements and contents thereof to the sterile medical implements. The isolation bag 165 is positioned in the dispensing chamber 151 and covers the sterile medical implements. It should be understood that the isolation bag 165 does not limit the passage of soiled medical implements into the dispensing chamber 151, rather, the isolation bag 165 partially covers the sterile medical implements, thereby isolating the sterile medical implements from the contents of the collection chamber 150. The open face 162 of the isolation bag 165 is sealed against either the body portion 110 or the dispenser lid 120. The isolation bag 165 is either permanently affixed or temporarily attached to the dispenser lid 120 or the body portion 110. For example, the periphery of the open face 162 of the isolation bag 165 is sandwiched between the bottom lip portion 146 and the topside of the dispenser lid 120. Alternatively or in addition to sandwiching the bag 165, the isolation bag 165 may be welded or adhered and thereby sealed to the body portion 110.

The enclosure 100' optionally includes a compressive spring 140 positioned between the collector lid 125 and the barrier tray 115. The compressive spring 140 exerts a force against the barrier tray to urge the barrier tray 115 to translate downward in response to the removal of sterile medical implements from the dispensing chamber 151. The compressive spring 140 limits the barrier tray 115 from binding with the interior walls of the body portion 110. The ends of the compressive spring 140 may either be releasably connected or welded to both the barrier tray 115 and the collector lid 125. The compression spring 140 may be used with or without the collection bag 160. A portion of the compression spring 140 is shown for purposes of clarity.

The enclosure 100' also optionally includes a tension spring 142 positioned between the dispenser lid 120 and the barrier tray 115. The tension spring 142 pulls upon the barrier tray 115 to urge the barrier tray 115 to translate downward in response to the removal of sterile medical implements from the dispensing chamber 151. Similar to the compression spring 140, the tension spring 142 limits the barrier tray 115 from binding with the interior walls of the body portion 110. The ends of the tension spring 142 may either be releasably connected or welded to both the barrier tray 115 and the dispenser lid 120. The tension spring 142 may be used with or without the isolation bag 165. A portion of the tension spring 142 is shown for purposes of clarity.

Regarding the assembly of the exemplary embodiment illustrated in FIG. 2, the casings 111 and 112 are snapped together to form body portion 110. The barrier tray 115 is inserted into the body portion 110 along the rails 147. A plurality of medical implements within the isolation bag 165 are positioned into the dispensing chamber 151. The open end 162 of the isolation bag 165 is welded to the bottom lip portion 146 of the body portion, thereby securing the isolation bag to the body portion 110. The dispenser lid 120 is snapped or welded onto the bottom lip portion 146 of the body portion 110 thereby encasing the medical implements. The body portion 110 is inverted and the collection bag 160 is placed into the collection chamber 150. The open end 161 of the collection bag 160 is welded to the top lip portion 145 of the body portion 110, thereby securing the collection bag 160 to the body portion 110. The collector lid 125 is snapped or welded onto the top lip portion 145 of the body portion 110 thereby substantially sealing the top end of the enclosure 100'. Although, this method of assembly is selected for description, other methods of assembling the enclosure 100' are contemplated.

Figure 3:
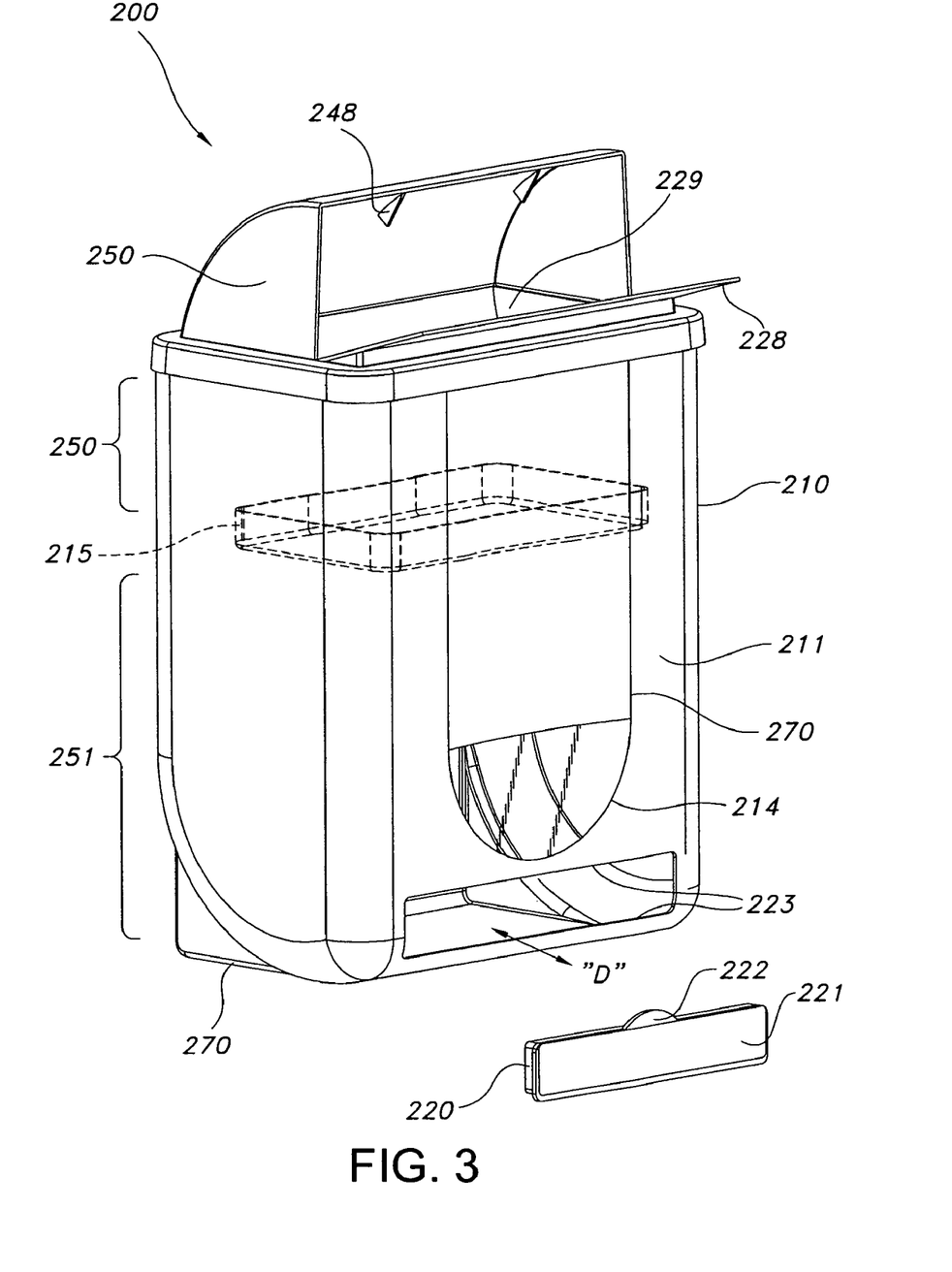
FIG. 3 is a front perspective view of yet another embodiment of a medical implement dispensing and disposal system according to an aspect of this invention.
Figure 4:
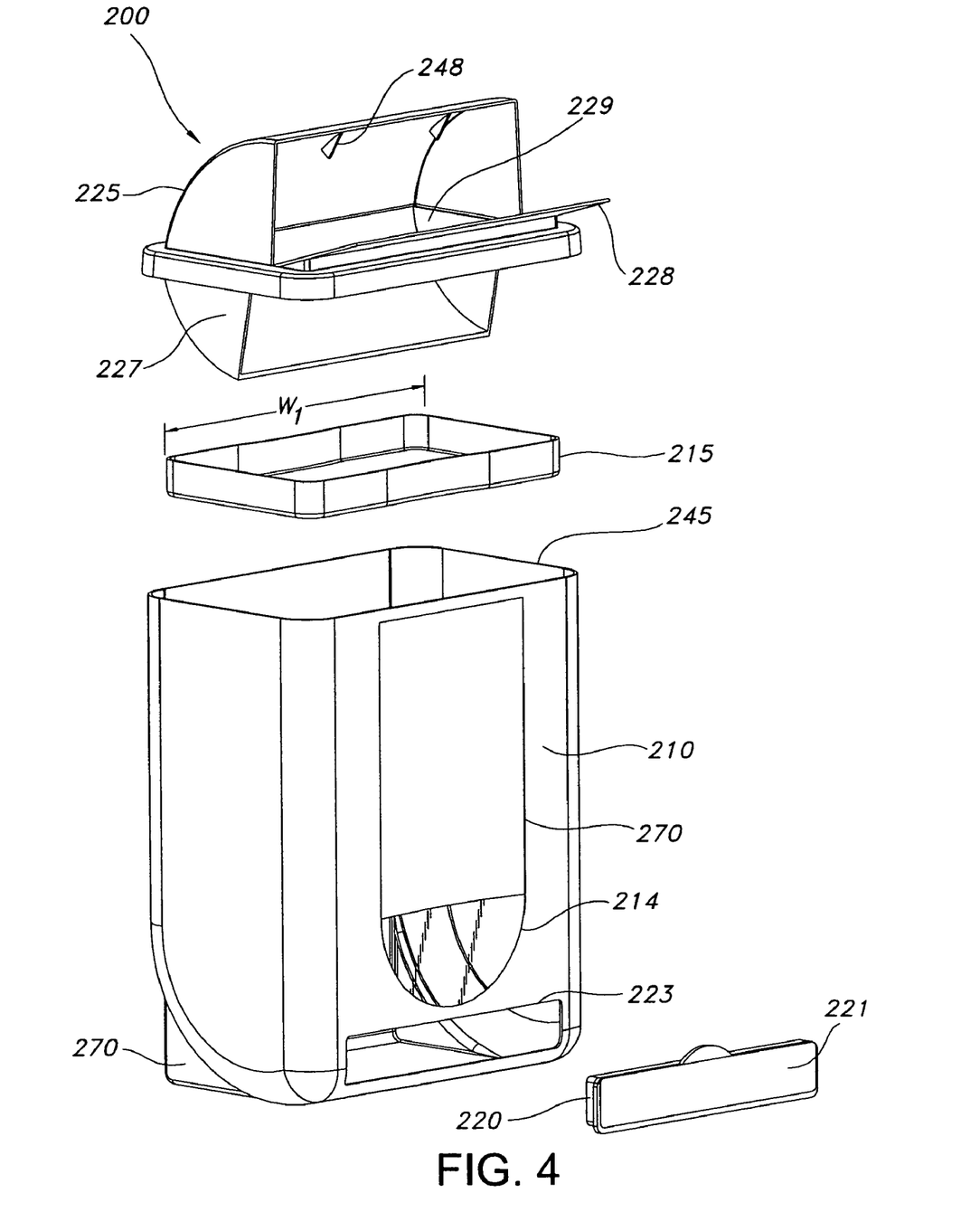
FIG. 4 is an exploded view of the system illustrated in FIG. 3.
Figure 5:
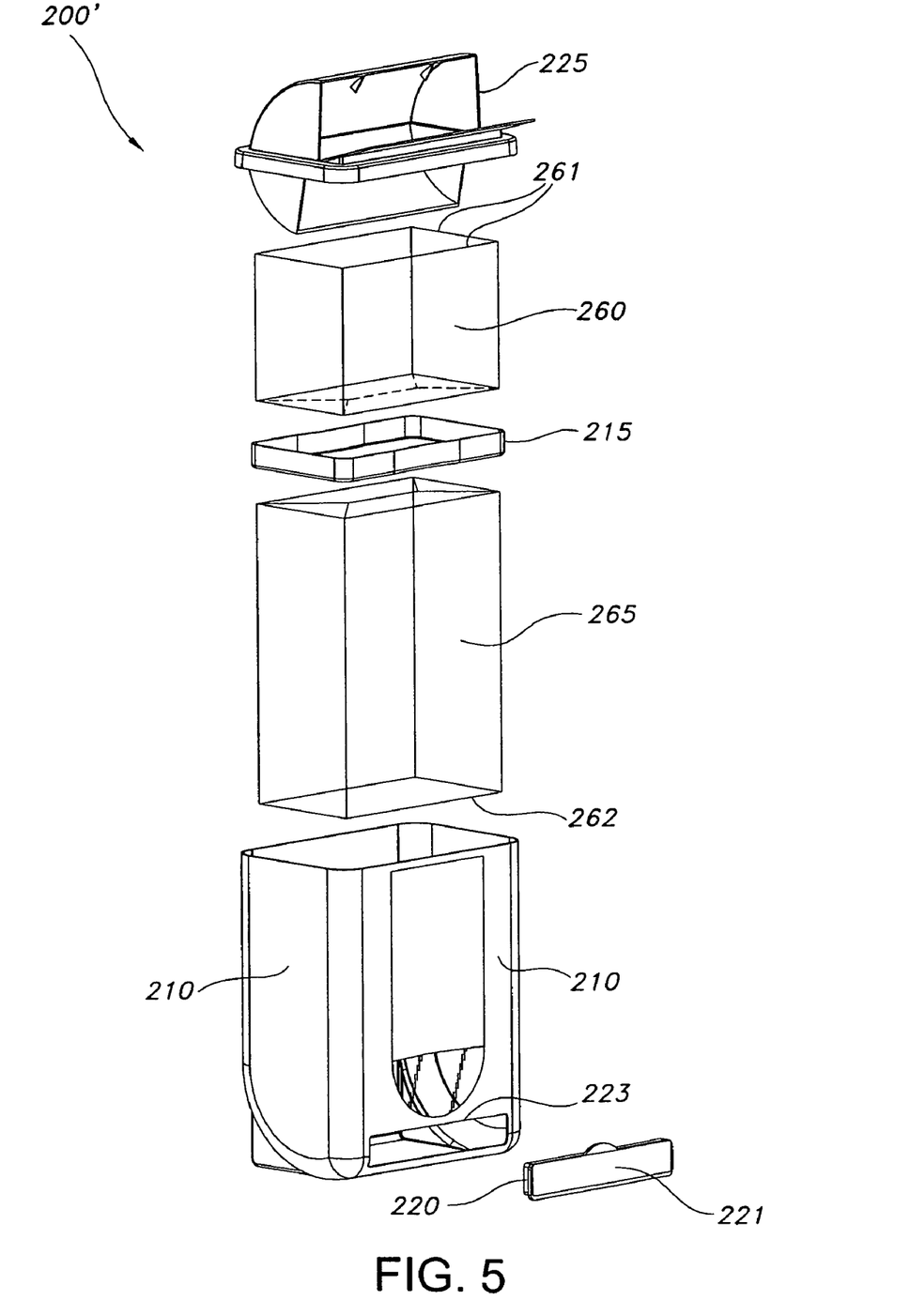
FIG. 5 is an exploded front perspective view of still another embodiment of a medical implement dispensing and disposal system according to an aspect of this invention.

Referring specifically to the embodiments illustrated in FIGS. 3, 4 and 5, medical implement dispensing and disposal enclosures according to other aspects of this invention are generally designated by the numerals 200 and 200'. The enclosure 200 is illustrated in FIGS. 3 and 4 and the enclosure 200' is illustrated in FIG. 5. Similar to the exemplary embodiment illustrated in FIGS. 1 and 2, the enclosures 200 and 200' generally include a body portion 210, a barrier tray 215 positioned within the interior of the body portion 210, a collector lid 225 mounted to the top end of the body portion 210, and a dispenser lid 220 mounted to the bottom end of the body portion 210. The collector lid 225 defines an inlet opening 229 and the body portion 210 defines an access opening 223. The openings 223, 229 are oriented in a forward facing direction "D", as illustrated in FIG. 3. A collection chamber 250 is maintained above the barrier tray 215 and a dispensing chamber 251 is maintained below the barrier tray 215.

The enclosure 200' optionally includes a collection bag 260 positioned above the barrier tray 215 to collect the soiled medical implements and an isolation bag 265 positioned below the barrier tray 215 to partially encase the sterile medical implements, as illustrated in FIG. 5. The enclosure 200' also optionally includes tension spring(s) 242 and compression spring(s) 240 positioned below and above the barrier tray 215, respectively. The springs 240 and 242 are not shown in the figures for the purposes of clarity.

The body portion 210 of the exemplary embodiments illustrated in FIGS. 3 through 5 differs from the body portion 110 illustrated in FIGS. 1 and 2. In the embodiments illustrated in FIGS. 3 through 5 the body portion 210 comprises a single unitary body. The seamless unitized body reduces the possibility of leakage through a seam. The body portion 210 provides an access opening 223 on the front wall 211. The access opening 223 is positioned on the lower end of the body portion 210 to provide access to the sterile medical implements within the dispensing chamber 251. The dispenser lid 220 mounts to the access opening 223 of the body portion 210. The dispenser lid 220 may be clipped, clamped, welded or adhered to the periphery of the access opening 223 or by any other mechanical fastening method known in the art.

The body portion 210 also provides at least two feet 270 positioned on the base of the body portion. The feet 270 are configured to maintain the enclosure 200, 200' in an upright position when the enclosure 200, 200' is mounted on a surface such as a floor or desk. The rear wall of the body portion 210 may also provide holes or protrusions to facilitate wall mounting of the enclosure 200, 200'. The body portion 210 of this exemplary embodiment is formed by a blow molding process. However, the body portion 210 may also be formed by an injection molding, casting, or any other forming process.

The dispenser lid 220 of the exemplary embodiments illustrated in FIGS. 3 through 5 differs from the dispenser lid 120 illustrated in FIGS. 1 and 2. In the exemplary embodiments, the dispenser lid 220 is mounted to the periphery of the access opening 223. The dispenser lid 220 includes a hingedly connected chute 221, which pivots between an open position (as illustrated in FIG. 3) and a closed position (as illustrated in FIGS. 4 and 5). In the open position the chute 221 provides access to the sterile medical implements within the dispensing chamber 251. In the closed position, the chute 221 limits access to the dispensing chamber 251. A tab 222 formed in the chute 221 accommodates a user's finger for pivoting the chute between the open and closed positions.

Figure 6:
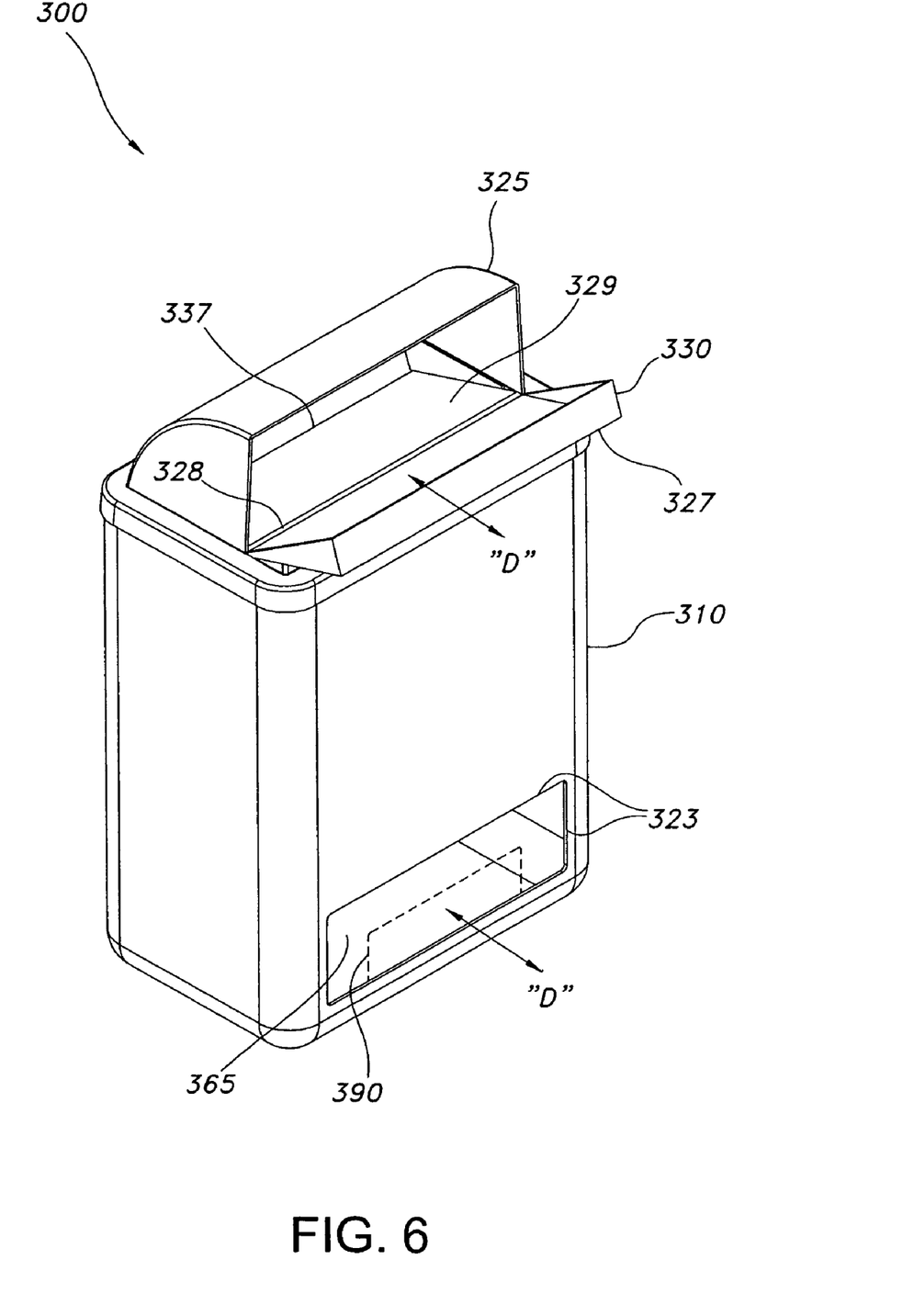
FIG. 6 is a front perspective view of another embodiment of a medical implement dispensing and disposal system according to an aspect of this invention.
Figure 7:
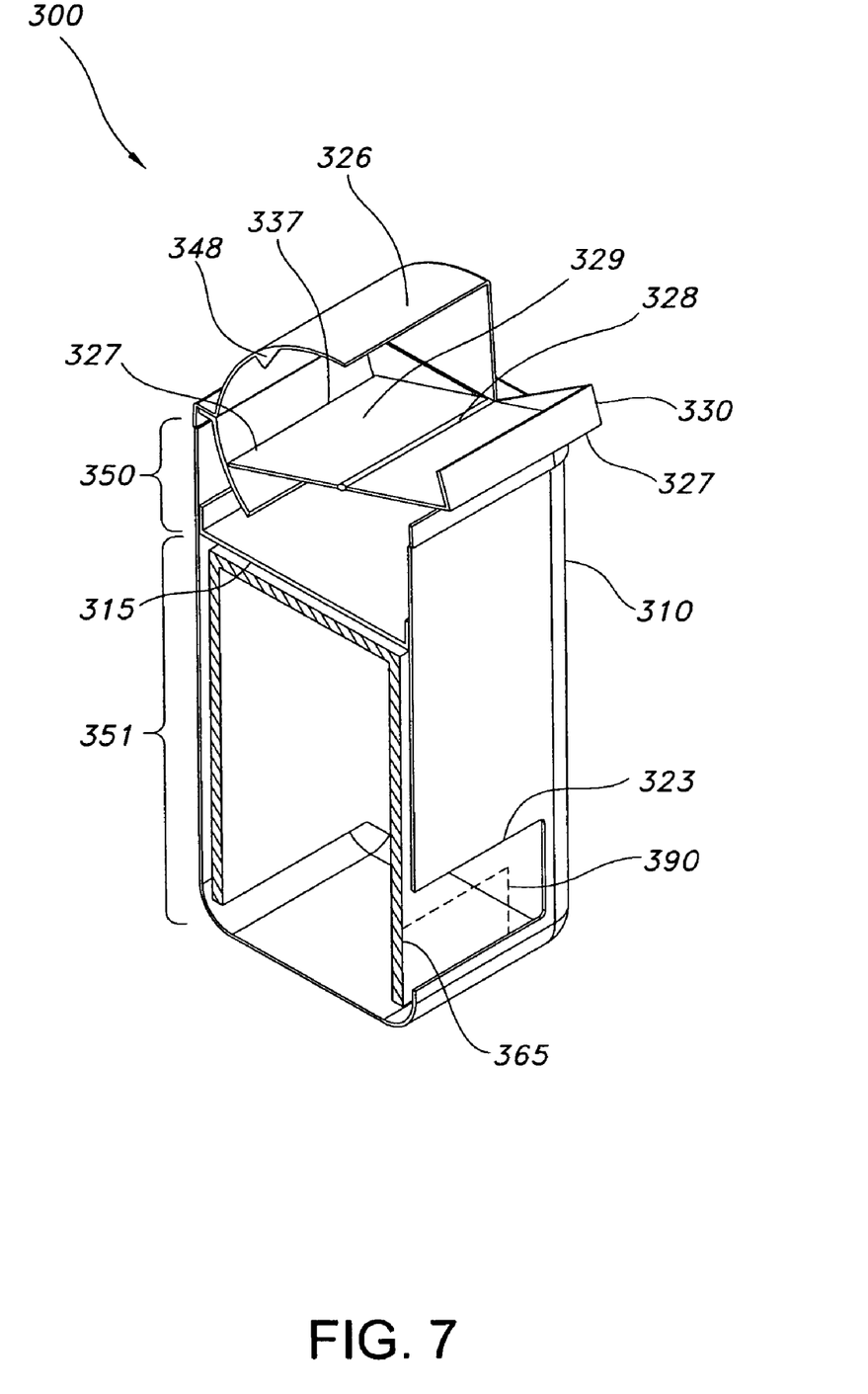
FIG. 7 is a cross-sectional front perspective view of the system illustrated in FIG. 6.

Referring specifically to the embodiment illustrated in FIGS. 6 and 7, a medical implement dispensing and disposal enclosure according to another aspect of this invention is generally designated by the numeral 300. Similar to the exemplary embodiments illustrated in FIGS. 3 through 5, the enclosure 300 includes a body portion 310, a barrier tray 315 positioned within the interior of the body portion 310 and a collector lid 325 mounted to the top end of the body portion 310. The collector lid 325 defines an access opening 329 for the passage of soiled medical implements into a collection chamber 350. The body portion 310 defines an access opening 323 positioned for the passage of sterile medical implements from the dispensing chamber 351. The openings 329, 323 are oriented in a forward facing direction "D", as illustrated in FIG. 6. The collection chamber 350 is maintained above the barrier tray 315 and a dispensing chamber 351 is maintained below the barrier tray 315. The collector lid 325 includes a hood portion 326 and a pivoting flip lid 327. An isolation bag 365 encloses the sterile medical implements and a collection bag 360 is positioned above the barrier tray 315. One or more optionally provided tension spring(s) 342 and compression spring(s) 340 are positioned below and above the barrier tray 315, respectively. The springs 340, 342 and the collection bag 360 are not shown in the Figures for the purposes of clarity.

The collector lid assembly 325 of the exemplary embodiment illustrated in FIGS. 6 and 7 differs from the collector lids illustrated in the previous embodiments. In this exemplary embodiment, the collector lid assembly 325 includes a pivoting flip lid 327 that pivots about a hinge 328. The rigid flip lid 327 comprises a rear portion 337, front portion 330 and a hinge portion linking the rear portion 337 to the front portion 330. The hinge 328 includes two extended flange portions that are inserted through holes provided in the hood portion 326 of the collector lid assembly 325 thereby captivating the flip lid 327 to the hood portion 326. By virtue of the hinge 328, the flip lid 327 is configured to pivot between an open position and a closed position (as illustrated in FIGS. 6 and 7).

In use, a soiled medical implement is placed on the rear portion 337 of the flip lid 327. The front portion 330 of the flip lid is rotated in a clockwise fashion thereby rotating the rear portion 337 into the interior of the collection chamber 350. By virtue of gravity, the soiled medical implement descends into the collection chamber and settles on top of the barrier tray 315. The flip lid 327 is then rotated in a counterclockwise fashion to return it to the closed position.

The body portion 310 of the exemplary embodiment illustrated in FIGS. 6 and 7 includes an access opening 323. In this embodiment, the isolation bag 365 provides a perforated strip 390 for the passage of sterile medical implements from the dispensing chamber 351 through the access opening 323. In use, the user tears the perforated strip 390 to access the sterile medical implements.

Regarding the packaging of the exemplary embodiments illustrated in FIGS. 1 through 7, the enclosure may be distributed with sterile medical implements pre-packaged within the dispensing chamber. Alternatively, the sterile medical implements may be packaged external to and along with the enclosure. In such case, the user would manually load the individual sterile medical implements into the dispensing chamber.

The sterile medical implements may be encased in a plastic bag or a hard or soft plastic case. The unused medical implements may be supplied on an interlinked roll wherein each pre-packaged medical implement is separated by a perforation. The interlinked roll of sterile medical implements would facilitate controlled sequential distribution of the medical implements from the trough portion. Accordingly, in use, the user tears the perforation to separate the individual medical implements. Alternatively, multiple sterile medical implements may be pre-packaged within a single bag.

Although this invention has been described with reference to particular embodiments selected for illustration in the figures, it will be appreciated that many variations and modifications can be made to the system 100, 100', 200, 200', 300 and the components thereof without departing from the spirit or the scope of this invention. For example, it should be noted that it is not required that the unused medical implements are sterile, as the dispensing chamber is configured to contain a medical implement in any condition. Additionally, although several molding processes are mentioned, the systems and components thereof are not limited to any specific manufacturing process.

What is claimed:

1. A medical implement dispenser and disposal system comprising:
   an enclosure having a body portion defining a vertical longitudinal axis;
   a dispensing chamber within the body portion configured to contain clean medical implements;
   a collection chamber within the body portion above the dispensing chamber along the vertical longitudinal axis and configured to collect soiled medical implements;
   the body portion defining an access opening positioned for passage of the clean medical implements from the dispensing chamber and the body portion further defining an inlet opening positioned for passage of the soiled medical implements into the collection chamber;
   a barrier positioned within the body portion, the barrier separating the dispensing chamber from the collection chamber, the barrier limiting the passage of the soiled medical implements from the collection chamber to the dispensing chamber;
   a spring cooperating with the barrier, wherein the spring translates the barrier in response to the passage of the clean medical implements from the dispensing chamber; and
   a first receptacle positioned above the barrier and configured to collect the soiled medical implements, the first receptacle further limiting the passage of the soiled medical implements into the dispensing chamber.

2. The medical implement dispenser and disposal system of claim 1 further comprising a second receptacle positioned below the barrier and configured to at least partially encase the clean medical implements.

3. The medical implement dispenser and disposal system of claim 1 further comprising a dispensing cover coupled to the body portion adjacent the access opening, the dispensing cover having an open position permitting dispensation of the clean medical implements through the access opening and a closed position inhibiting dispensation of the clean medical implements through the access opening.

4. The medical implement dispenser and disposal system of claim 1 further comprising an inlet cover coupled to the body portion adjacent the inlet opening, the inlet cover having an open position for passage of the soiled medical implements through the inlet opening and a closed position inhibiting passage of the soiled medical implements through the inlet opening.

5. The medical implement dispenser and disposal system of claim 1, the barrier having a wall with a width and a height, wherein a ratio of the height to the width is about 0.23:1 or greater.

6. The medical implement dispenser and disposal system of claim 1, the barrier having a wall with a width and a height, wherein a ratio of the height to the width is about 0.25:1 or greater.

7. The medical implement dispenser and disposal system of claim 1, the barrier including an indicator positioned to indicate positioning of the barrier to thereby provide information regarding content of the dispensing chamber and the collection chamber.

8. The medical implement dispenser and disposal system of claim 7, the body portion including a substantially translucent window positioned to permit visualization of the indicator.

9. The medical implement dispenser and disposal system of claim 1 wherein the dispensing chamber is positioned within the body portion of the enclosure such that the clean medical implements are urged from the dispensing chamber by gravity.

10. A medical implement dispenser and disposal system comprising:
an enclosure having a body portion;
a dispensing chamber within the body portion configured to contain medical implements;
a collection chamber within the body portion above the dispensing chamber and configured to collect soiled medical implements;
the body portion defining an access opening positioned for passage of medical implements from the dispensing chamber and the body portion further defining an inlet opening positioned for passage of the soiled medical implements into the collection chamber;
a barrier positioned within the body portion, the barrier separating the dispensing chamber from the collection chamber, the barrier limiting the passage of the soiled medical implements from the collection chamber to the dispensing chamber;
a spring cooperating with the barrier, wherein the spring translates the barrier in response to the passage of medical implements from the dispensing chamber; and
an inlet cover coupled to the body portion adjacent the inlet opening, the inlet cover having an open position for passage of the soiled medical implements through the inlet opening and a closed position inhibiting passage of the soiled medical implements through the inlet opening, the inlet cover including a hood portion extending above the body portion and a cowl portion extending into the body portion, wherein the hood portion and the cowl portion are positioned to limit unauthorized access into said collection chamber.

11. The medical implement dispenser and disposal system of claim 10, the inlet cover further comprising a gate mounted to pivot between an open position and a closed position, wherein the gate obstructs the access opening in the closed position.

12. A method of providing a supply of medical implements and a receptacle for soiled medical implements comprising the steps of:
providing an enclosure defining along a vertical longitudinal axis;
positioning a barrier within the enclosure thereby dividing the enclosure into a collection chamber configured to collect soiled medical implements and a dispensing chamber configured to contain sterile medical implements whereby the collection chamber is positioned above the dispensing chamber along the vertical longitudinal axis;
positioning a first receptacle within the collection chamber and above the barrier to collect the soiled medical implements and limit the passage of the soiled medical implements from the first receptacle to the dispensing chamber and;
positioning a spring above the barrier to control translation of the barrier within the enclosure.

13. The method of claim 12 further comprising the step of adhering a periphery of the first receptacle to the enclosure.

14. The method of claim 12 further comprising the step of welding a periphery of the first receptacle to the enclosure.

15. The method of claim 12 further comprising the step of positioning a second receptacle below the barrier to enclose the sterile medical implements and limit the passage of the soiled medical implements from the collection chamber to the dispensing chamber such that comingling of the soiled medical implements and the sterile medical implements is minimized.

16. A medical implement dispenser and disposal system comprising:
an enclosure having a body portion defining a vertical longitudinal axis;
a dispensing chamber within the body portion configured to contain clean medical implements;
a collection chamber within the body portion above the dispensing chamber alone the vertical longitudinal axis and configured to collect soiled medical implements;
the body portion defining an access opening positioned for passage of the clean medical implements from the dispensing chamber and the body portion further defining an inlet opening positioned for passage of the soiled medical implements into the collection chamber, wherein the body portion includes a front casing, a rear casing, an upper lid, and a lower lid configured and dimensioned for engagement such that the body portion defines an enclosed interior space;
a barrier positioned within the body portion, the baffler separating the dispensing chamber from the collection chamber, the barrier limiting the passage of the soiled medical implements from the collection chamber to the dispensing chamber; and
a spring cooperating with the barrier, wherein the spring translates the barrier in response to the passage of the clean medical implements from the dispensing chamber.

17. The medical implement dispenser and disposal system of claim 16 wherein the front casing and the rear casing are substantially identical in structure.

* * * * *